(12) United States Patent
Murrell et al.

(10) Patent No.: US 10,856,942 B2
(45) Date of Patent: Dec. 8, 2020

(54) SYSTEM AND METHOD FOR CLOSED-LOOP SURGICAL TOOL HOMING

(71) Applicant: Ethicon LLC, Guaynabo, PR (US)

(72) Inventors: Niko Murrell, Blue Ash, OH (US); David Perdue, Montgomery, OH (US)

(73) Assignee: Ethicon LLC, Guaynabo, PR (US)

(*) Notice: Subject to any disclaimer, the term of this patent is extended or adjusted under 35 U.S.C. 154(b) by 272 days.

(21) Appl. No.: 15/910,550

(22) Filed: Mar. 2, 2018

(65) Prior Publication Data
US 2019/0269465 A1   Sep. 5, 2019

(51) Int. Cl.
*A61B 34/20*   (2016.01)
*A61B 18/00*   (2006.01)
*A61B 34/30*   (2016.01)

(52) U.S. Cl.
CPC .............. *A61B 34/20* (2016.02); *A61B 18/00* (2013.01); *A61B 34/30* (2016.02); *A61B 2018/00595* (2013.01); *A61B 2034/2065* (2016.02); *A61B 2560/0223* (2013.01)

(58) Field of Classification Search
CPC ......... A61B 34/20; A61B 34/30; A61B 18/00; A61B 2034/2065; A61B 2018/00595; A61B 2560/0223
See application file for complete search history.

(56) References Cited

U.S. PATENT DOCUMENTS

| 7,386,365 B2* | 6/2008 | Nixon ..................... A61B 34/35 700/245 |
| 7,930,065 B2* | 4/2011 | Larkin .................... B25J 19/025 700/245 |
| RE43,952 E * | 1/2013 | Uhl ........................ A61B 90/10 600/424 |
| 8,771,270 B2 | 7/2014 | Burbank |
| 8,831,782 B2 | 9/2014 | Itkowitz |
| 9,055,961 B2 | 6/2015 | Manzo et al. |
| 9,492,240 B2* | 11/2016 | Itkowitz ................. A61B 90/06 |
| 9,526,587 B2* | 12/2016 | Zhao ...................... A61B 90/94 |
| 9,549,781 B2* | 1/2017 | He ..................... A61B 17/00234 |
| 9,731,415 B2* | 8/2017 | Lohmeier .......... A61B 1/00149 |
| 10,299,883 B2* | 5/2019 | Kilroy .................... A61B 34/25 |
| 10,327,854 B2* | 6/2019 | Overmyer .............. A61B 34/71 |
| 10,413,366 B2* | 9/2019 | Dyer ...................... G16H 40/63 |

(Continued)

FOREIGN PATENT DOCUMENTS

| WO | 2014151621 A1 | 9/2014 |
| WO | 2014151952 A1 | 9/2014 |
| WO | 2015125914 A1 | 8/2015 |

*Primary Examiner* — Harry Y Oh
*Assistant Examiner* — George Sun
(74) *Attorney, Agent, or Firm* — Mintz Levin Cohn Ferris Glovsky and Popeo, P.C.

(57) ABSTRACT

An exemplary system and method for homing a surgical tool are provided. In general, a surgical tool can include an end effector, an elongate shaft, and a wrist that couples the end effector to a distal end of the shaft can be configured to facilitate movement of the end effector relative to the shaft. The surgical tool can be coupled to a robotic surgical system featuring an imaging device and a processor. Through the use of closed-loop feedback and machine vision techniques, the end effector can be calibrated into a home position to ensure precise and accurate movement of the end effector when in use by a surgeon.

13 Claims, 7 Drawing Sheets

(56) References Cited

U.S. PATENT DOCUMENTS

| | | | |
|---|---|---|---|
| 10,485,617 B2* | 11/2019 | Crawford | A61B 46/20 |
| 10,555,775 B2* | 2/2020 | Hoffman | A61B 5/06 |
| 2004/0236316 A1 | 11/2004 | Danitz et al. | |
| 2005/0149003 A1* | 7/2005 | Tierney | A61B 34/71 |
| | | | 606/1 |
| 2005/0251110 A1* | 11/2005 | Nixon | A61B 34/37 |
| | | | 606/1 |
| 2007/0156019 A1* | 7/2007 | Larkin | B25J 19/025 |
| | | | 600/104 |
| 2008/0221732 A1* | 9/2008 | Toth | G16H 40/40 |
| | | | 700/245 |
| 2009/0202387 A1 | 8/2009 | Dlugos, Jr. et al. | |
| 2010/0168562 A1* | 7/2010 | Zhao | A61B 90/94 |
| | | | 600/426 |
| 2014/0005640 A1 | 1/2014 | Shelton, IV et al. | |
| 2015/0094737 A1 | 4/2015 | Hatakeyama | |
| 2016/0213224 A1 | 7/2016 | Hatakeyama et al. | |
| 2016/0374772 A1* | 12/2016 | Hasegawa | A61B 34/37 |
| | | | 606/130 |
| 2018/0000543 A1 | 1/2018 | Hibner | |
| 2019/0060008 A1* | 2/2019 | Bailey | A61B 34/20 |

\* cited by examiner

SYSTEM AND METHOD FOR CLOSED-LOOP SURGICAL TOOL HOMING

FIELD

Systems and methods are provided for using closed-loop feedback and machine vision to home a surgical tool.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Current robotic systems typically include a tool having an elongate shaft with an end effector configured to be introduced into a patient's body, e.g., through a trocar or other access device. The tool is mounted on an electromechanical robotic arm assembly that is coupled to a control system for controlling the robotic arm assembly and the tool. One drawback to current robotic systems is that it can be difficult to know the exact position of the end effector. For example, an end effector having an articulation joint or wrist can be positioned at an articulation angle that is not precisely known by the system. Although homing methods have been proposed, existing methods are mechanical in structure and can be challenging to incorporate into a robotic system. Additionally, existing methods do not allow the user to confirm that the end effector is accurately homed after the homing process has been completed.

Accordingly, there remains a need for improved methods and systems for homing a surgical tool.

SUMMARY OF THE INVENTION

In general, methods and systems for homing a surgical tool are provided. The methods and systems described herein can utilize machine vision techniques and closed-loop feedback to precisely and accurately calibrate the location/position of a surgical tool to ensure accurate movement of the end effector of the surgical tool during surgical procedures. Use of machine vision techniques allows for accurate and precise calibration without the use of additional hardware, and use of closed-loop feedback allows the user of the surgical tool to confirm with certainty that the surgical tool is properly calibrated.

In one embodiment, a system for calibrating the position of a surgical tool is provided and includes a surgical tool having an actuator and an end effector, at least one imaging device, and a processor. The end effector can have at least one target feature, and the surgical tool can store a reference data set which includes reference positional information of the at least one target feature. The at least one imaging device can be configured to acquire at least one image containing actual positional information of the at least one target feature. The processor can be configured to electronically receive the reference data set from the surgical tool and the actual positional information from the at least one imaging device, detect a discrepancy between the actual positional information of the at least one target feature and the reference positional information of the at least one target feature, generate a transformation instruction from the discrepancy, and cause the actuator to move the end effector in response to the transformation instruction.

In certain embodiments, the system can include an electromechanical robotic arm having a tool carrier on a distal end thereof that is configured to couple to a housing of the surgical tool. The processor can be coupled to the electromechanical robotic arm and it can be configured to control movement of the electromechanical robotic arm and the surgical tool. In other aspects, the processor can be coupled to the imaging device and can be configured to cause the imaging device to acquire images containing actual positional information of the at least one target feature.

The target feature(s) can have a variety of configurations. For example, the target feature(s) can be a point, a line, a ridge, a joint location, an axis of rotation, a grip position, a surgical tool outline, a surgical tool form, a surgical tool edge, a surgical tool surface, a surgical tool shape, a surgical tool region color, a fiducial, a laser marking, a pad printed marking, a molded element, a machined element, or combinations thereof. In certain embodiments, the at least one target feature can include at least two target features on the end effector.

The end effector can also have a variety of configurations. For example, the end effector can be forceps, graspers, a needle driver, a clamp, scissors, an electrocautery tool, a circular stapler, a box stapler, a clip applier, a suction tool, an irrigation tool, a linear stapler, a suture stitching device, and a vessel sealer.

In other embodiments, the surgical tool can be a first surgical tool and the reference data set can be a first reference data set including reference positional information of the at least one target feature of the first surgical tool. The system can further include a second surgical tool having at least one target feature and a second reference data set including reference positional information of the at least one target feature of the second surgical tool. The first reference data set can differ from the second reference data set.

In another embodiment, a surgical tool is provided that includes a housing, an elongate shaft extending distally from the housing, an end effector on a distal end of the elongate shaft and having at least one target feature, an actuator extending between the housing and the end effector and configured to actuate the end effector, and a memory in one of the housing, the elongate shaft, and the end effector. The memory can store a reference data set including reference positional information for the at least one target feature on the end effector.

The housing can have a variety of configurations. In one embodiment, the housing can be configured to couple to a robotic system such that the reference data set can be transferred to the robotic system, and a transformation instruction can be received from the robotic system. The transformation instruction can be based on a discrepancy between actual positional information of the at least one target feature and the reference positional information of the at least one target feature. The actuator can be configured to move in response to receipt of the transformation instruction from the robotic system to thereby reposition the end effector based on the transformation instruction.

The end effector can have a variety of configurations, and can be any one of forceps, graspers, a needle driver, a clamp, scissors, an electrocautery tool, a circular stapler, a box stapler, a clip applier, a suction tool, an irrigation tool, a linear stapler, a suture stitching device, and a vessel sealer. The target feature can also have a variety of configurations, and can be any one of a point, a line, a ridge, a joint location, an axis of rotation, a grip position, a surgical tool outline, a surgical tool form, a surgical tool edge, a surgical tool surface, a surgical tool shape, a surgical tool region color, a fiducial, a laser marking, a pad printed marking, a molded element, a machined element, or combinations thereof. In some aspects, the at least one target feature can include at least two target features on the end effector.

In another aspect, a method of calibrating a position of an end effector of a surgical tool is provided, and can include coupling a surgical tool to a surgical robotic system such that a reference data set including reference positional information of at least one target feature on an end effector of the surgical tool is transmitted from the surgical tool to a computing device of the surgical robotic system. The processor can perform a calibration test that includes obtaining at least one image containing actual positional information of the at least one target feature on the end effector, generating a transformation function based on the reference positional information and the actual positional information, and sending the transformation function to the surgical tool to cause an actuator of the surgical tool to reposition the end effector to a repositioned location based on the transformation function.

In certain embodiments, the method can include, prior to performing the calibration test, positioning the end effector within a body cavity of a patient.

In other aspects, the method can include decoupling the surgical tool from the surgical robotic system, and coupling a second surgical tool to the surgical robotic system such that a second reference data set, which differs from the first reference data set, is transmitted from the surgical tool to the surgical robotic system.

In another embodiment, the actual positional information can include actual positional information of the at least one target feature on the end effector within the body cavity. The at least one target feature on the end effector can be, for example, any one of a point, a line, a ridge, a joint location, an axis of rotation, a grip position, a surgical tool outline, a surgical tool form, a surgical tool edge, a surgical tool surface, a surgical tool shape, a surgical tool region color, a fiducial, a laser marking, a pad printed marking, a molded element, a machined element, and combinations thereof.

In other embodiments, the method can include obtaining at least one post-calibration image containing post-calibration location information of the at least one target feature and confirming that the post-calibration location information is substantially the same as the reference positional information.

BRIEF DESCRIPTION OF DRAWINGS

This invention will be more fully understood from the following detailed description taken in conjunction with the accompanying drawings, in which.

DETAILED DESCRIPTION

Figure 1A:
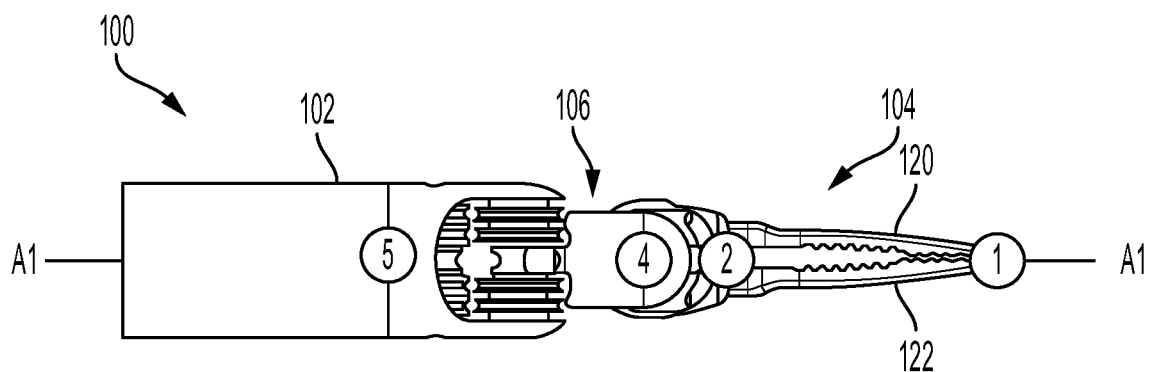
FIG. 1A is a perspective view of a distal portion of a surgical tool with a clamp end effector which features several exemplary locations for target features.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and systems for homing a surgical tool are provided. In general, a surgical tool can include an elongate shaft and an end effector at a distal end of the shaft. The end effector can have a variety of configurations for treating tissue, and the surgical tool can include any number of actuators for actuating various features on the end effector, such as jaw opening/closing, articulation, shaft or end effector rotation, firing, etc. Each actuator can rotate and/or translate through the elongate shaft for actuating the end effector. To confirm a precise position or movement of the end effector, such as an articulation angle, a rotation angle, a jaw position, etc., the end effector can include any number of target features which can be detected by an imaging device used in conjunction with the surgical tool. The tool can have a memory that stores a reference data set which contains information, referred to as reference positional information, relating to the target feature(s) on the end effector. When the tool is coupled to a surgical robotic system, the reference data set can be transmitted to the system. The system can use the imaging device to detect actual positional information of the target feature(s) on the end effector, and the system can compare the actual positional information to the reference data set to determine whether any discrepancies exist. If a discrepancy is detected, the system can generate a transformation instruction which can cause movement of the end effector to correct the discrepancy. In this way, the system can ensure that the end effector is positioned properly and precisely in accordance with any actuation instructions. In an alternative embodiment, the transformation instruction can correct the robots computer model that is based on the reference data.

The systems and methods disclosed herein can be used in conjunction with any surgical tool having various end effector configurations. By way of non-limiting example, end effectors can include forceps, graspers, a needle driver, a clamp, scissors, an electrocautery tool, a circular stapler, a box stapler, a clip applier, a suction tool, an irrigation tool, a linear stapler, a suture stitching device, a vessel sealer, etc.

Figure 1B:
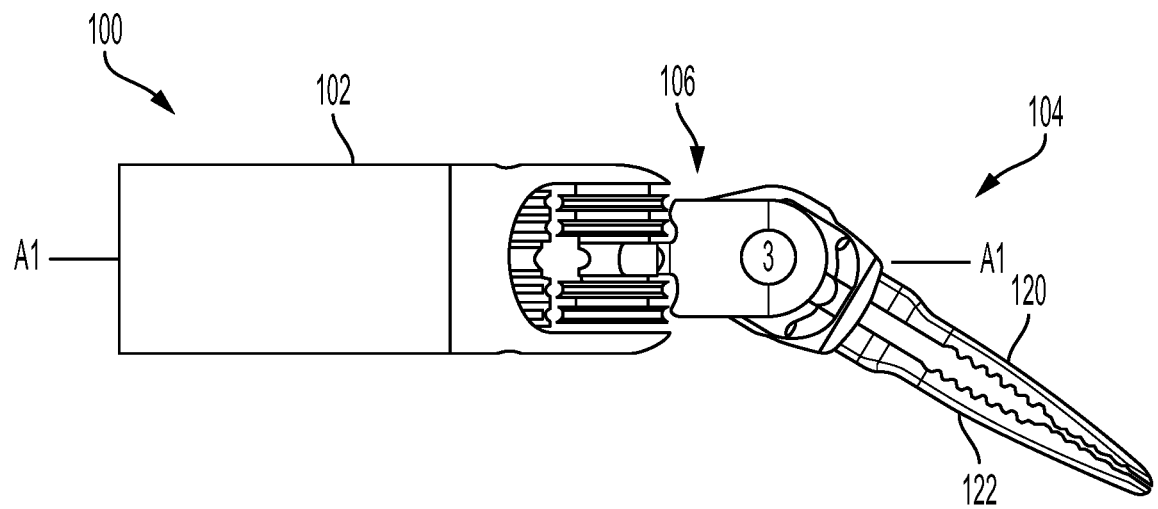
FIG. 1B is a perspective view of the distal portion of the surgical tool of FIG. 1A, shown in an articulated position.

FIGS. 1A-1B illustrate one exemplary embodiment of a distal portion of a surgical tool 100 having a clamp end effector 104. As shown, the tool 100 includes an elongate shaft 102 (also referred to herein as a "shaft" and a "tool shaft"), an end effector 104, a wrist 106 at a distal end of the shaft 102 that couples the end effector 104 to the shaft 102, and a tool housing (not shown) coupled to a proximal end of the shaft 102.

While the end effector 104 can have a variety of configurations, in the illustrated embodiment the end effector 104 includes a pair of opposed jaws 120, 122 that are movable between opened and closed positions for grasping tissue therebetween. Each jaw 120, 122 is pivotable at the wrist 106 for moving between the open and closed positions. The jaws 120, 122 can also pivot as a unit to allow the entire end effector 104 to articulate, as shown in FIG. 1B.

The wrist 106 can have any of a variety of configurations. In general, the wrist 106 can include a joint configured to allow movement of the clamp end effector 104 relative to the shaft 102, such as a pivot joint at which the jaws 120, 122 of the clamp end effector 104 are pivotally attached. In some embodiments, the pivoting motion can include pitch movement about a first axis of the wrist 106 (e.g., a X axis), yaw movement about a second axis of the wrist 106 (e.g., a Y axis), and combinations thereof to allow for 360° rotational movement of the clamp end effector 104 about the wrist 106. In other embodiments, the pivoting motion can be limited to movement in a single plane, e.g., only pitch movement about the first axis of the wrist 106 or only yaw movement about the second axis of the wrist 106, such that clamp end effector 104 articulates in a single plane.

The housing can include various actuators extending through the elongate shaft 102 and coupled to the end effector 104 for controlling the operation of various features associated with the end effector 104 (e.g., any one or more of clamping, firing, rotation, articulation, energy delivery, etc.). The actuators can translate or rotate to drive one or more actions on the end effector 104, such as shaft rotation, end effector rotation, end effector articulation, jaw opening/closing, etc. In at least some embodiments, the housing can be configured to releasably couple to a robotic surgical system, as will be discussed in more detail below, and the tool housing can include coupling features configured to allow the control system to control motion of the actuators and thus the tool.

Further details on the illustrated tool 100 and the robotic system are disclosed in U.S. application Ser. No. 15/200,283 entitled "Methods, Systems, and Devices for Initializing a Surgical Tool," filed on Jul. 1, 2016, International Patent Publication No. WO 2014/151952 entitled "Compact Robotic Wrist" filed on Mar. 13, 2014, and International Patent Publication No. WO 2014/151621 entitled "Hyperdexterous Surgical System" filed on Mar. 13, 2014, which are hereby incorporated by reference in their entireties.

As indicated above, the surgical tool 100 can include at least one target feature for use in calibrating or homing the surgical tool, as discussed in further detail below. Examples of such a target feature include various markings, such as a point or a line, surface features such as a protrusion or a ridge, or features on the end effector such as a joint location, an axis of rotation, a grip position, a surgical tool outline, a surgical tool form, a surgical tool edge, a surgical tool surface, a surgical tool shape, or a surgical tool region color. The target feature(s) can also include a fiducial. Examples of a fiducial include a laser marking, a pad printed marking, a molded element, and a machined element.

The target features that are included as part of the surgical tool can vary with the type of end effector attached to the tool. Some types of target features are capable of being used with all types of end effectors, while other types of target features are specific to the type of end effector used in the surgical tool.

Where the target feature is in the form of a marking or surface feature, the location can vary depending on the configuration of the end effector and what position is being determined, i.e., the articulated and/or clamped position of the jaws, the rotational position of the shaft and/or the end effector, etc. For example, if the target feature is used to indicate the articulation angle of the end effector relative to the elongate shaft, the target feature can be located at or adjacent to the articulation joint. Where the target feature is used to identify a position of one or both jaws, the target feature can be located at the pivot joint or wrist, or it can be located on the jaws. FIGS. 1A and 1B illustrate various exemplary regions that can be associated with one or more target features for identifying positions such as the tip position 1, the grip parallelism 2, the axis angular position 3, the joint position location 4, and the shaft to wrist interface 5.

With regard to the tip position 1, the tip on each jaw 120, 122 can be detected by an imaging system using edge detection software. By determining the location of each tip relative to the elongate shaft, the system can identify the articulation angle of the entire end effector 104 relative to an axis of the elongate shaft 102, and/or the articulation angle of each jaw 120, 122 relative to an axis of the elongate shaft 102. The system can thus confirm whether the end effector 104 is in an initial zero-angle position or is at an angular orientation, and/or it can identify the clamping position of each jaw 120, 122, e.g., fully opened, fully closed, or at a position between opened and closed.

In other aspects, the edge 2 of the jaws 120, 122 can form a target feature, and the system can detect each edge 2 to determine whether the jaws 120, 122 are parallel or non-parallel. This determination can be used to indicate the amount of opening/closing of the jaws 120, 122.

In other embodiments, as shown in FIG. 1B, the pivot joint 3 about which the end effector 104 rotates can form a target feature that can be used to determine the articulation angle of the end effector 104. For example, the pivot joint 3 itself, or features thereon or therearound, can be detected by the imaging system and used to indicate the rotational position or articulation angle of the end effector 104.

The location 4 of the pivot joint within the patient's body relative to other components of the tool 100 or relative to the patient or other tools used in the system, can be used to indicate the position of the end effector 104.

In other aspects, the shaft to wrist interface 5 can be used to indicate, for example, the rotational position of the end effector 104 relative to the shaft 102. For example, the relative positions of the components on each side of the interface 5, or markings or features on one or both sides of the interface 5, can indicate the rotational orientation.

A person skilled in the art will appreciate that the target feature(s) can have a variety of forms at various locations depending on the configuration of the tool and end effector. The target feature(s) can be features already present on the end effector, such as any shape, edge, joint, etc. of the end effector or tool, or the target feature(s) can be features added to the end effector to aid in visual identification of the feature using an imaging device, as will be discussed in more detail below.

Figure 1C:
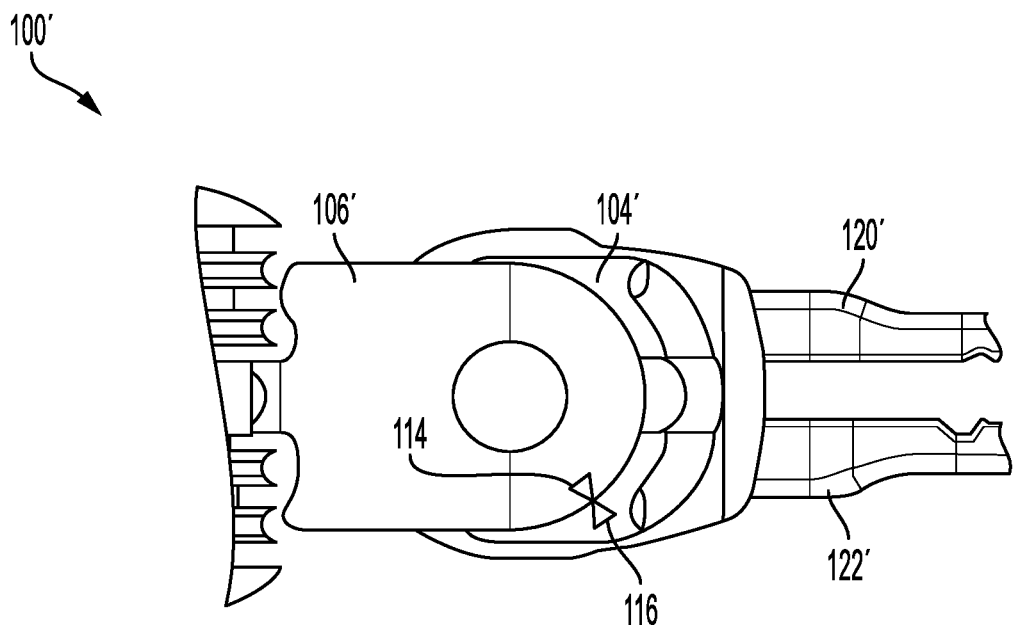
FIG. 1C is a perspective view of the distal portion of the surgical tool of FIG. 1A, showing fiducials as a target feature.
Figure 1D:
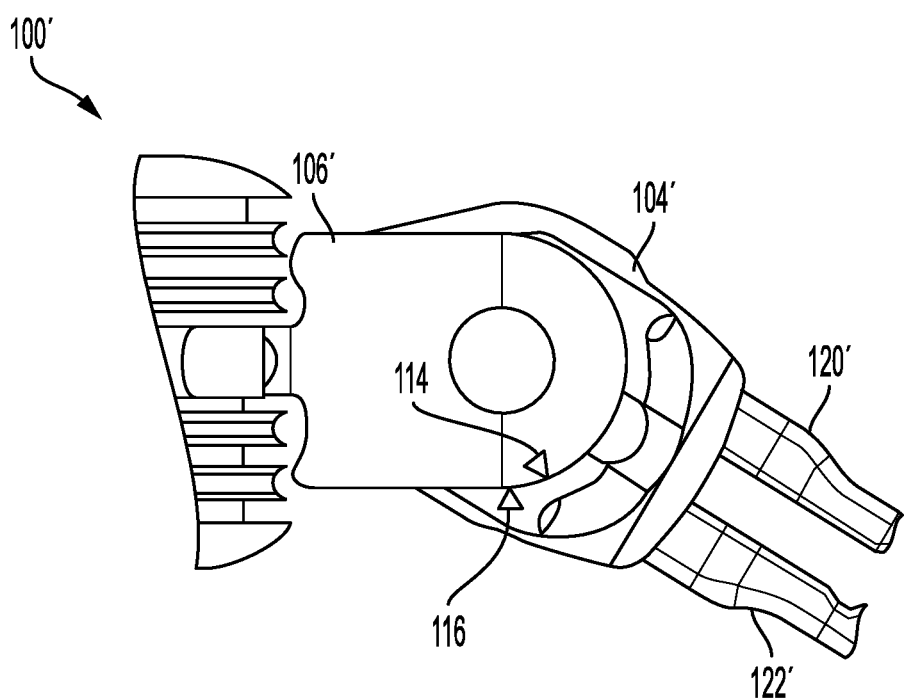
FIG. 1D is a perspective view of the distal portion of the surgical tool of FIG. 1C, shown in an articulated position.

In another embodiment, the target feature(s) can be in the form of a fiducial which provides a point of reference or measure. FIGS. 1C-1D illustrate a distal portion of a surgical tool 100' that has the same configuration as tool 100, but that includes fiducials 114, 116. The fiducials 114, 116 can indicate, for example, the degree of articulation of the clamp end effector 104'. FIG. 1C shows a first fiducial 114 on the wrist 106' of the tool 100' and a second fiducial 116 on the clamp end effector 104', with the first and second fiducials 114, 116 being aligned when the clamp end effector 104' is in an initial, unarticulated zero angle position. FIG. 1D shows the clamp end effector 104' articulated such that it extends at a transverse, non-zero angle relative to the main body or shaft 102 of the tool 100', and as a result the second fiducial 116 is offset from the first fiducial 114. The fiducials 114, 116 can be detected by an imaging device and used to indicate a degree of articulation of the clamp end effector 104', thereby allowing the system to confirm the precise position of the clamp end effector 104'. Where the system controls the position of the end effector 104', the system can control the actuators to position the end effector 104' in a desired position, and then use the imaging device to identify whether the actual position as detected by the imaging device corresponds with the position as instructed by the control system. While not shown, in other embodiments the fiducials 114, 116 can be located on one of the jaws 120', 122' and the housing or body adjacent to the jaw to thereby indicate a position of the jaws 120', 122'. Any of positions 1-5 as identified in FIGS. 1A-1B can include fiducials, or other positions as may be desired based on the particular end effector.

A person skilled in the art will appreciate that while the illustrated fiducials 114, 116 are in the form of triangular-shaped arrows, the fiducials can have any configuration and any number of markings can be used. For example, the wrist 106' can include multiple markings or features, such as lines or protrusions, which can correspond to a predetermined degree of articulation. Thus, alignment of the fiducial 116 on the end effector 102' with the fiducial 114 the wrist 106' can indicate a particular articulation angle.

As indicated above, the tools can be used in various surgical robotic systems. By way of non-limiting example, one embodiment of a robotic surgical system is described in U.S. Pat. No. 8,831,782 entitled "Patient-Side Surgeon Interface for a Teleoperated Surgical Instrument" filed Jul. 15, 2013, which is hereby incorporated by reference in its entirety. Other embodiments of surgical robotic systems are disclosed in aforementioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, which are incorporated by reference herein in their entireties. Also, exemplary embodiments of a tool housing of a surgical tool including one or more actuators and being configured to releasably attach to a surgical robotic system are described in International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, which are incorporated by reference herein in their entireties.

Figure 2:
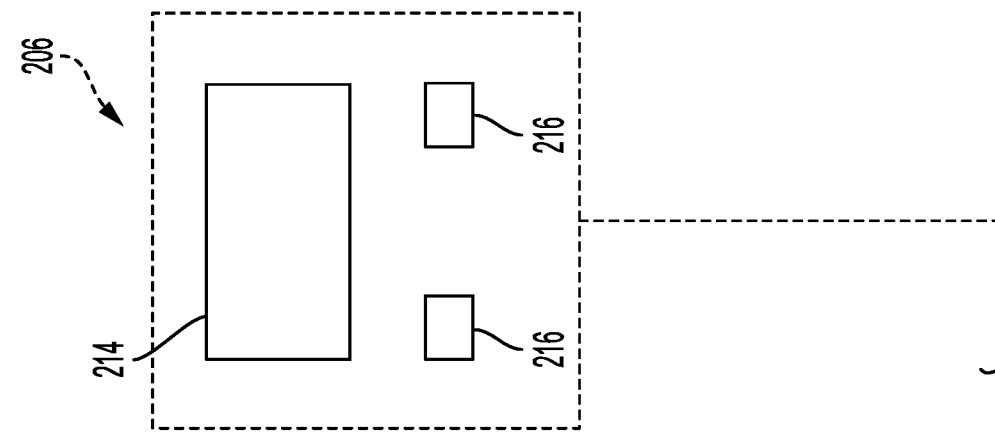
FIG. 2 is a perspective view of one embodiment of a surgical robotic system that includes a patient-side portion and a user-side portion.
Figure 2:
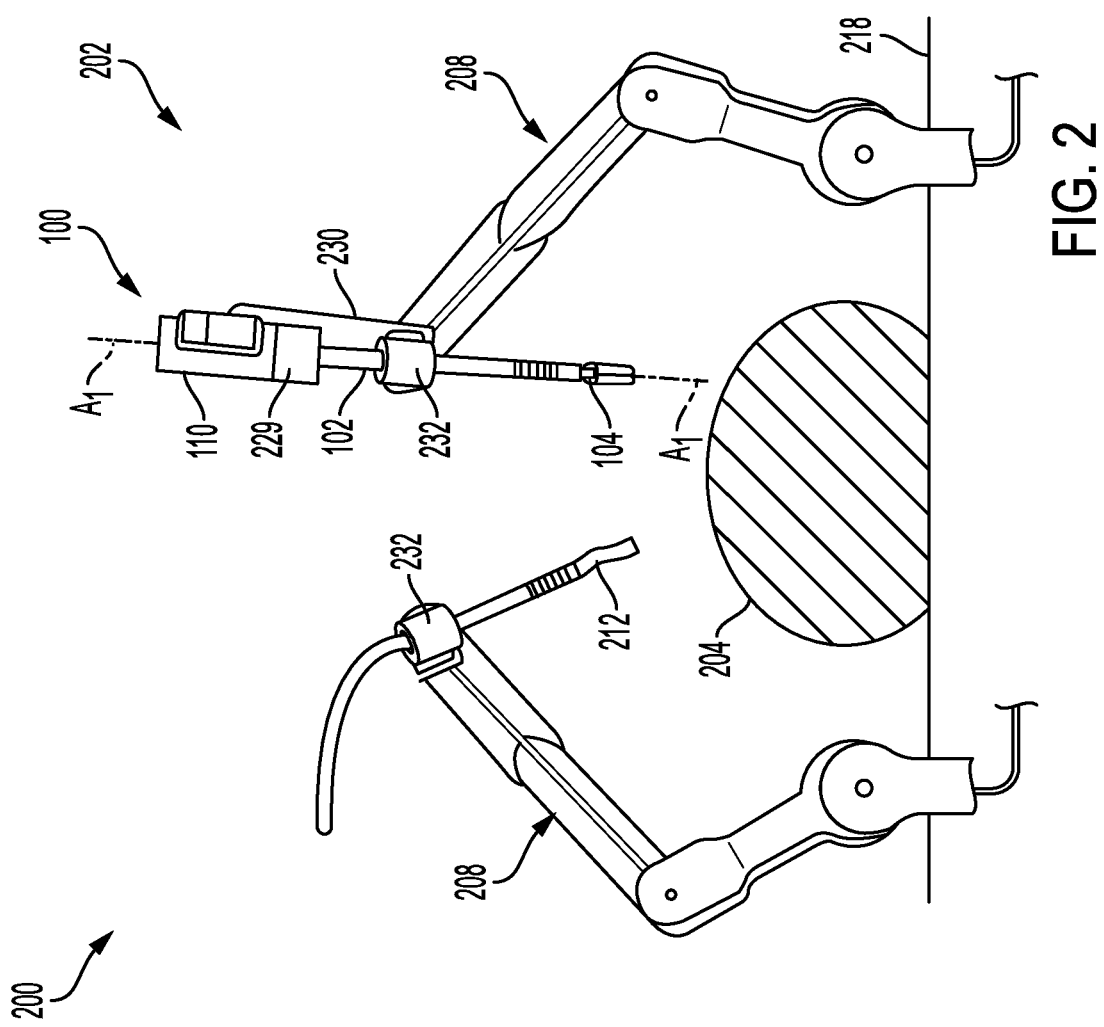

FIG. 2 shows one exemplary embodiment of a surgical robotic system 200 that includes a patient-side portion 202 that is positioned adjacent to a patient 204, and a user-side portion 206 that is located a distance from the patient, either in the same room and/or in a remote location. The patient-side portion 202 generally includes one or more electromechanical robotic arms 208 (two arms are shown) and one or more surgical tools 100 (one tool is shown) that are configured to releasably couple to the electromechanical robotic arms 208. The patient-side portion 202 can include an imaging device 212, e.g., an endoscope, for obtaining images of the tools within the surgical site in the patient 204. The user-side portion 206 generally includes a control system 214 for controlling the robotic arms 208, tools 100, and imaging device 212. The user-side portion 206 can also include one or more user input devices 216 for receiving an input from a user to control movement of the electromechanical robotic arms 208, surgical tools 100, and/or imaging device 212 during a surgical procedure. A person skilled in the art will appreciate that the surgical robotic system can have a variety of configurations.

As illustrated in FIG. 2 the patient-side portion 202 is coupled to an operating table 218. However, in other embodiments, the patient-side portion 202 can be mounted to a wall, to the ceiling, to the floor, or to other operating room equipment. Further, while the patient-side portion 202 is shown as including two electromechanical robotic arms 208, more or fewer electromechanical robotic arms 208 may be included. Furthermore, the patient-side portion 202 can include separate robotic arms 208 mounted in various positions, such as relative to the operating table 218. Alternatively, the patient-side portion 202 can include a single assembly that includes one or more electromechanical robotic arms 208 extending therefrom.

As will be discussed in more detail below, the patient-side portion 202 can also include any number of tools 100, which can be coupled to an electromechanical robotic arm 208, as shown in FIG. 2. Where the tool 100 is coupled to an electromechanical robotic arm 208, the arm 208 can include one or more linkages with a tool carrier 230 on a distal end thereof. The tool carrier 230 can include a trocar 232 coupled to a distal end thereof and a tool driver 229 movably coupled to a proximal end thereof. The tool driver 229 can couple to the tool housing 110 such that the elongate shaft 102 of the tool 100 extends through the trocar 232 and into the patient 204. The tool driver 229 can include motors therein for engaging and driving the various tool actuators of the tool 100. The motors can be operatively coupled to the control system 214, e.g., wired or wirelessly, such that the control system can actuate the motors to thereby drive the actuators in the tool 100.

The control system 214 can also have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 214 can be configured to perform various functions and to control various components of the system. For example, the control system 214 can be configured to receive user input instructions from one or more user input devices 216, and to transfer those instructions to patient-side portion 202 to cause movement of the robotic arm(s) 208 and/or to actuate the tool 100 for performing a procedure. In some embodiments, the user input device 216 can include one or more manually-operated input devices, such as a joystick, exoskeletal glove, a powered and gravity-compensated manipulator, or the like. The one or more user input devices 216 can control teleoperated motors which, in turn, control the movement of the electromechanical robotic arms 208 and surgical tool 100.

As explained in more detail below, in certain embodiments the control system 214 can be configured to receive information from the surgical tool 100 coupled to the robotic arm 208. This information can include tool-specific information that may be helpful in controlling actuation of the tool 100. In an exemplary embodiment, the information can include a reference data set which contains information relating to the target feature(s) on the surgical tool 100. This information, referred to herein as reference positional information, provides the control system 214 with details that enable the control system 214 to visually detect and precisely locate the target feature(s) on that tool for the purpose of determining whether the tool is accurately positioned. In particular, the reference positional information provides the control system 214 with the position information (size, shape, location, orientation, tolerance criteria, etc.) for each target feature. In other words, the reference positional information includes information relating to where each target feature should be located when the end effector is in a particular orientation. This allows the control system to detect whether a position of the tool and/or end effector, as determined from an actual image of the target feature(s), is identical to the position of the tool and/or end effector as indicated by the reference positional information. The reference positional information can also include tolerance criteria for indicating when the tool is positioned within an accepted tolerance range relative to the reference positional information.

The control system 214 can also be configured to perform a homing procedure, in which the control system obtains an image, using the imaging device 212, of the target feature(s) on the tool 100 to thereby identify the actual location of the target feature(s) on the tool 100. This can be performed manually be a user or automatically by the control system 214, the it can be performed either prior to or during a surgical procedure with the tool 100 positioned external to or within the patient. The information obtained from the images taken by imaging device 212 by the control system 214 is referred to herein as actual positional information. The control system can compare the actual positional information to the reference positional information and determine whether any discrepancies exist. If discrepancies are present, the control system 214 can generate instructions, referred to herein as a transformation instruction, that can cause the tool 100 to be repositioned, thereby correcting for the discrepancy. As a result, the control system 214 can identify the actual position of the tool or end effector on the tool and, by comparing this information to the reference positional information that identifies what the actual position of the tool should be, the system 214 can determine whether the tool is properly homed or whether corrections need to be made. In an alternative embodiment, the transformation instruction can correct the robots computer model that is based on the reference data.

Figure 3:
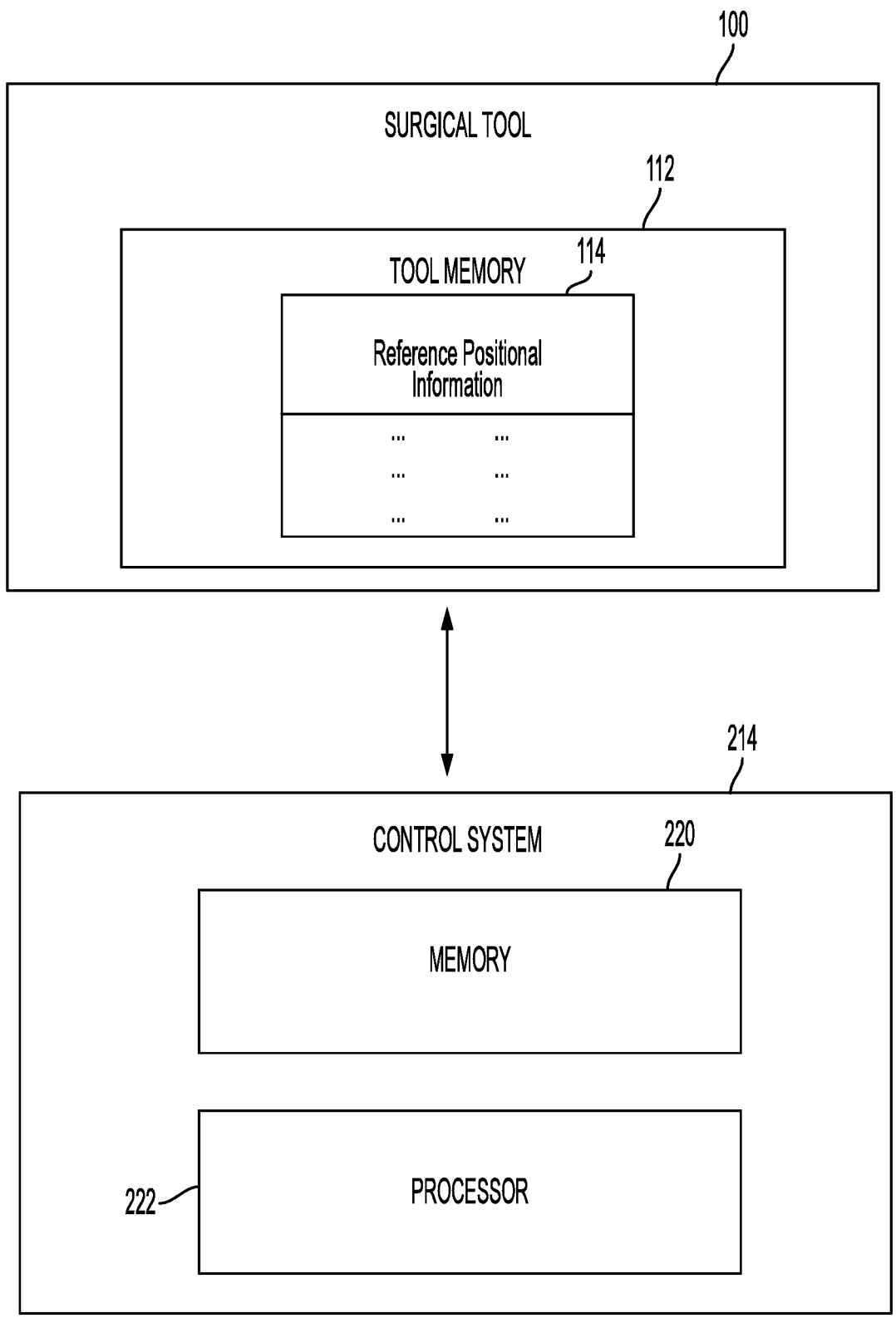
FIG. 3 is a block diagram schematically showing the surgical tool having a tool memory, and showing the control system having memory and a processor.

FIG. 3 schematically illustrates the tool 100 coupled to control system 214. As shown, the tool 100 can include a memory 112 for storing reference positional information 124 of the target feature(s) of the surgical tool 100. The memory 112 can be located anywhere on the tool 100, such as in the tool housing 110 or in the end effector 104. The memory 112 can be any suitable computer readable medium configured to store computer-executable instructions. The control system 214 can also include a memory 220 and at least one processor 222. The memory 220 and the processor 222 can be included in a suitable computing device that can be part of the control system 214 or that can be a remote computing device configured to communicate with the control system 214. The processor 222 can be configured to access the tool memory 112 for obtaining the reference positional information 124, and the processor 222 can be configured to execute the computer-executable instructions to perform various functions. It should be appreciated that the control system 214 can include various other components that are not shown in FIG. 3 for the sake of clarity.

Figure 4A:
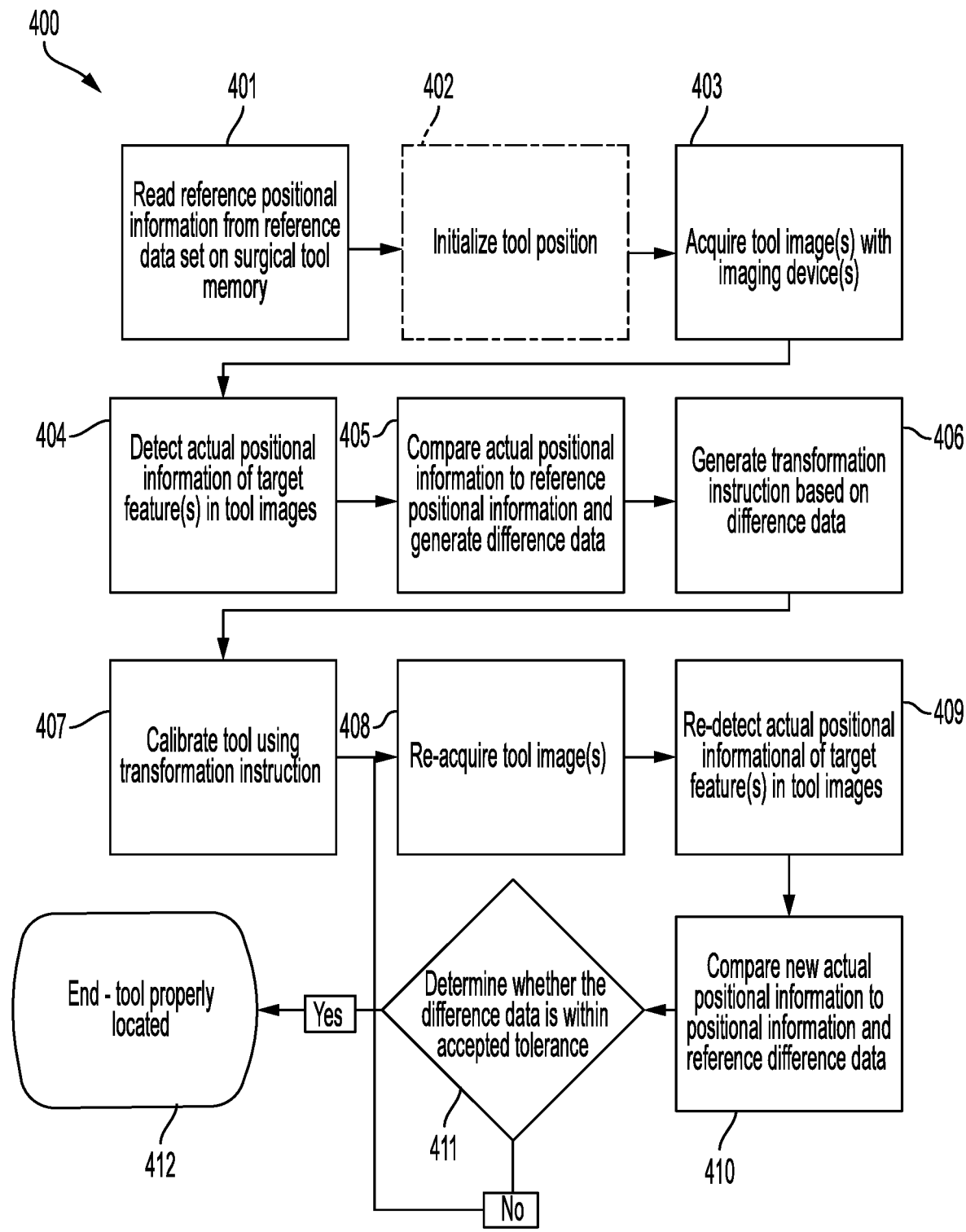
FIG. 4A is a block diagram illustrating a closed-loop method for calibrating a position of a tool with the use of machine vision techniques.

As indicated above, a calibration method is provided that utilizes machine vision techniques to home a surgical tool. FIG. 4A illustrates one exemplary embodiment of a calibration method 400. As shown in FIG. 4A, once the tool is connected to the surgical robotic arm, in step 401 the processor 222 receives or obtains the data set from the tool 100 which contains the reference positional information 124 for the target feature(s) of the surgical tool 100. As previously stated, the data set containing the reference positional information 124 can be stored in the tool memory 112. The reference positional information 124 can also be stored in the memory 220 of the robotic surgical system 214, or it can be stored in the memory of another computing device, for use by the processor 222.

In a further step 402, the surgical tool 100 can be manipulated to position the target feature(s) on the tool 100 within the view of the imaging device 212. This may be referred to herein as "initialization." The surgical tool 100 can be initialized either by manually positioning the tool as desired, or utilizing the control system 214 which controls the motors and linkage members to position the robotic arm 208 and/or the tool 100 and end effector 104. Manipulation can include positioning the tool shaft 102, the end effector 104, and/or the jaws 120, 122 of the end effector 104 in a particular rotation and/or angular position. Initialization is deemed successful when the target feature(s) are within the field of view of the imaging device 212. In other embodiments, initialization need not be performed, particularly where a generalized three-dimensional position transformation is developed. In particular, multiple imaging devices can be used to detect and identify the precise location of the tool and tool components within a three-dimensional space.

In a further step 403, the imaging device 212 is activated and at least one image of the tool 100 is acquired. Activation of the imaging device 212 can occur either manually by the user or by the control system 214. The tool 100 can remain stationary during imaging, or the tool 100 can be moved into various positions by the control system 214 during imaging, allowing the imaging device 212 to capture a continuous images or a series of images.

Figure 4B:
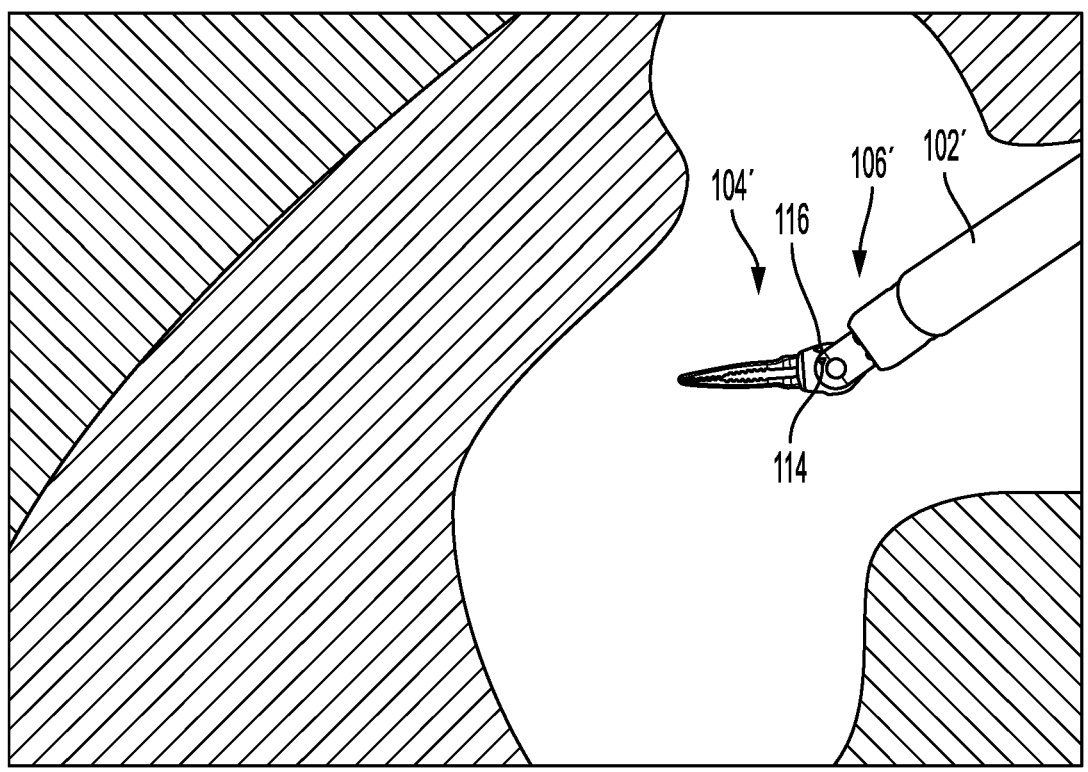
FIG. 4B is an illustration of a photographic image of a tool within a patient's body cavity.

By way of non-limiting example, the tool 100' as shown in FIG. 1C can be present in an image, as shown in FIG. 4B. In this embodiment, prior to obtaining the image, the control system can control the actuators to position the tool at a zero-degree articulation angle, i.e., so that the end effector 104' is longitudinally aligned with the shaft 102'.

Once the image(s) are obtained, in a further step 404, the processor 222 can read the image(s) and, using machine vision techniques known to one having ordinary skill in the art, detect the presence of the target feature(s) in the images and determine the actual positional information of the target feature(s). Examples of machine vision techniques that could be used to determine the actual positional information include edge detection, color analysis, blob detection and extraction, pattern recognition, and optical character recognition.

With reference to FIG. 4B, the control system 214 can process the image to detect the location of the target feature 114 on the wrist 106' and the target feature 116 on the jaws 104'. This information can be used to generate the actual positional information.

In a further step 405, the processor 222 can compare the reference positional information of the target feature(s) and to the actual positional information, for example by applying numerical analysis techniques to discern the differences between the actual positional information of the target feature(s) and the reference positional information of the target feature(s). Examples of the difference between the actual positional information and reference positional information can include a difference in angle or position between fiducials 114, 116, a difference in position of the tip of the clamp end effector 104, a difference in angular position of the end effector 104 relative to the tool shaft 102, and a difference in the position of wrist 106.

In the embodiment shown in FIG. 4B, the offset position of the target feature 116 on the jaws 104' as compared to the target feature 114 on the wrist 106' indicates that a discrepancy exists. In other words, while the control system positioned the end effector 104' at a zero-degree articulation angle and the reference positional information informs the control system that the target features 114, 116 should be aligned in such a position, the image indicates that an offset is present and the target features 114, 116 are not positioned according to the reference positional information.

In a further step 406, the processor 222 can generate a transformation instruction. The transformation instruction can be based on a measured error or difference/discrepancy between the actual positional information and the reference positional information. With reference to FIG. 4B, the transformation instruction would correspond to an instruction for the end effector 104' to move by an amount equivalent to the offset between the target features 114, 116 and in a direction opposite from the direction of offset.

In a further step 407, the transformation instruction can be sent to the actuator(s) on the tool 100 to adjust the position of the tool 100 and/or the end effector 104, such as, e.g., the pitch and/or yaw angle of the clamp end effector 104 relative to the tool shaft 102, the rotational position of the end effector 104 relative to the tool shaft 102, the angular position of each jaw 120, 122 relative to one another and/or to the tool shaft 102, etc. When sent to the tool 100, the transformation instruction can cause the surgical tool 100 to be re-positioned into a position that is approximately the same as the desired reference position embodied by the reference positional information 124 of the target feature(s). In other words, the transformation instruction corrects the position of the tool 100. For example, if, in step 405, the processor 222 compares the angular position of the clamp end effector 104 relative to the tool shaft 102 embodied by the reference positional information to the actual positional information obtained using the imaging device 212 and determines, in step 406, that the difference in angular position between the two is something other than zero, the processor will generate a transformation instruction that instructs the actuator to pivot the end effector 104 such that the difference in angular position between the two is approximately zero. The system is thus positioning the end effector in a position that corresponds with the reference positioned information, thereby homing the tool to correct for any discrepancies. In certain embodiments, the transformation instructions may only be generated if the discrepancy is outside of a certain tolerance range.

In the embodiment shown in FIG. 4B, the transformation instruction causes the end effector 104' to move in a downward direction in the image by an amount equal to the offset between the target features 114, 116, thereby causing the end effector 104' to be properly positioned at the zero-degree, non-articulated position.

In a further step 408, after the tool 100 is repositioned such that the position of the end effector 104 is approximately the same as it is in the desired reference position, at least one additional image of the surgical tool 100 can be acquired by the imaging device 212.

In steps 409 and 410, the process of detecting the actual positional information of the target feature(s) in the tool image(s), and comparing the new actual positional information to the reference positional information 124 to generate difference data is repeated.

In a further step 411, the processor 222 analyzes the updated difference data to assess whether the difference between the actual position of the target feature(s) and the reference position of the target feature(s) exceeds acceptable, pre-determined tolerance criteria obtained or received from the tool memory 112. If the difference does not exceed the tolerance criteria, the calibration process is complete because the surgical tool 100 has been properly calibrated, and the actual position of the target feature(s) is substantially the same as the reference position of the target feature(s) (see 412). However, if the updated difference data exceeds the tolerance criteria, the processor 222 will re-execute steps 408-411 until the difference between the post-calibrated position of the target feature(s) and the reference position of the target feature(s), as embodied by the reference positional information 124 of the target feature(s), has met the tolerance criteria.

All of the aforementioned steps can be implemented using a closed loop system, whereby the system actively obtains images, detects discrepancies, and makes adjustments accordingly to thereby properly position the tool.

The systems and methods disclosed herein can be implemented using one or more computer systems. One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer system having a display device, such as for example a cathode ray tube (CRT) or a liquid crystal display (LCD) or a light emitting diode (LED) monitor for displaying information to the user and a keyboard and an input device, e.g., a mouse, a trackball, a hand tracker, a gesture recognition device (e.g., Kinect), etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 5:
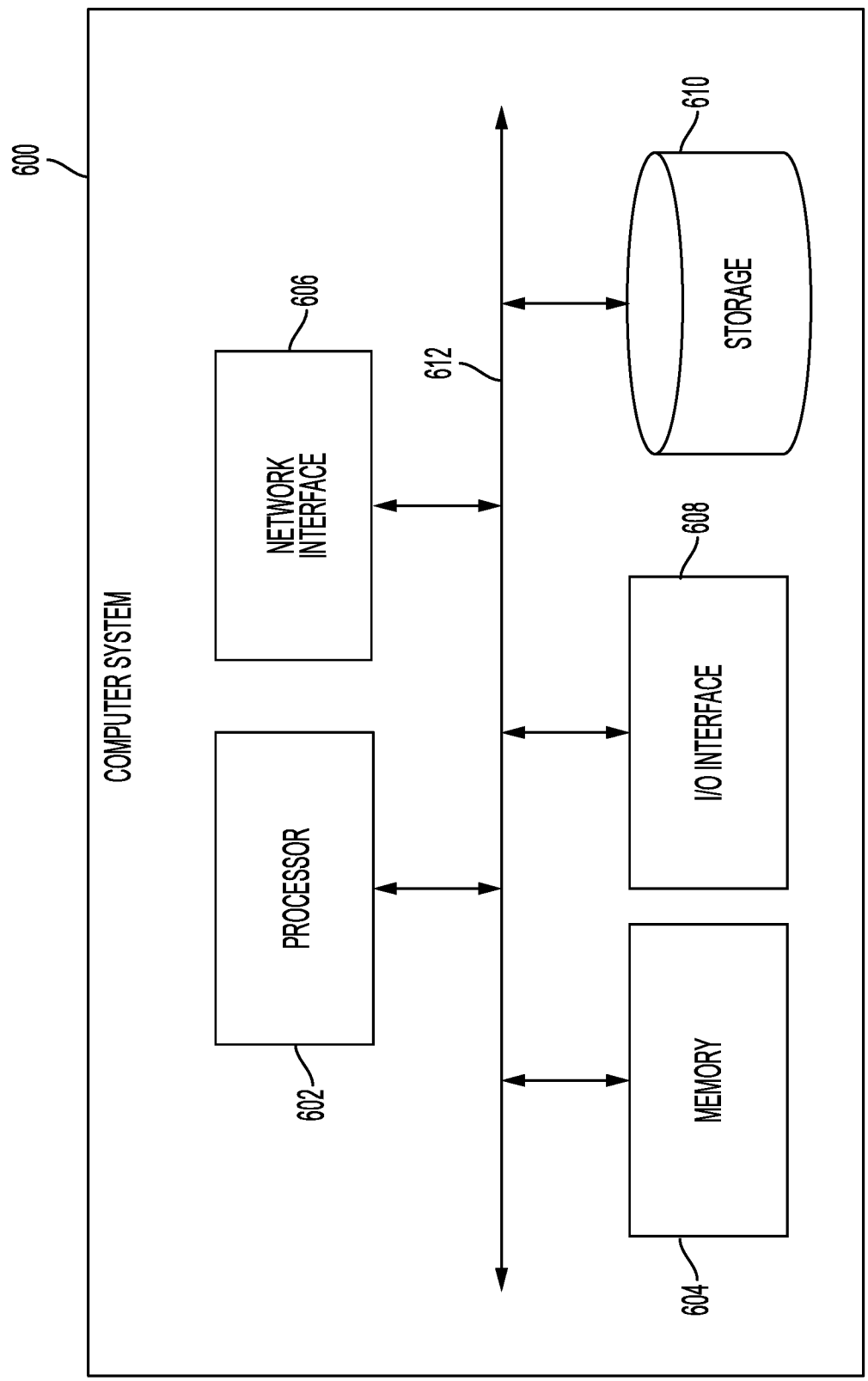
FIG. 5 is a block diagram illustrating a computer system for use in implementing the disclosed system and methods.

FIG. 5 illustrates one exemplary embodiment of a computer system 600. As shown, the computer system 600 can include one or more processors 602 which can control the operation of the computer system 600. "Processors" are also referred to herein as "controllers." The processor(s) 602 can include any type of microprocessor or central processing unit (CPU), including programmable general-purpose or special-purpose microprocessors and/or any one of a variety of proprietary or commercially available single or multi-processor systems. The computer system 600 can also include one or more memories 604, which can provide temporary storage for code to be executed by the processor(s) 602 or for data acquired from one or more users, storage devices, and/or databases. The memory 604 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 600 can be coupled to a bus system 612. The illustrated bus system 612 is an abstraction that represents any one or more separate physical busses, communication lines/interfaces, and/or multi-drop or point-to-point connections, connected by appropriate bridges, adapters, and/or controllers. The computer system 600 can also include one or more network interface(s) 606, one or more input/output (TO) interface(s) 608, and one or more storage device(s) 610.

The network interface(s) 606 can enable the computer system 600 to communicate with remote devices, e.g., other computer systems, over a network, and can be, for non-limiting example, remote desktop connection interfaces, Ethernet adapters, and/or other local area network (LAN) adapters. The IO interface(s) 608 can include one or more interface components to connect the computer system 600 with other electronic equipment. For non-limiting example, the IO interface(s) 608 can include high speed data ports, such as universal serial bus (USB) ports, 1394 ports, Wi-Fi, Bluetooth, etc. Additionally, the computer system 600 can be accessible to a human user, and thus the IO interface(s) 608 can include displays, speakers, keyboards, pointing devices, and/or various other video, audio, or alphanumeric interfaces. The storage device(s) 610 can include any conventional medium for storing data in a non-volatile and/or non-transient manner. The storage device(s) 610 can thus hold data and/or instructions in a persistent state, i.e., the value is retained despite interruption of power to the computer system 600. The storage device(s) 610 can include one or more hard disk drives, flash drives, USB drives, optical drives, various media cards, diskettes, compact discs, and/or any combination thereof and can be directly connected to the computer system 600 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 5 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 600 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 600 can also include a web server for generating and/or delivering the web pages to client computer systems.

In an exemplary embodiment, the computer system 600 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the systems and methods described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the instrument is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

In the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems- and methods, such dimensions are not intended to limit the types of shapes that can be used in conjunction with such systems and methods. A person skilled in the art will recognize that an equivalent to such linear and circular dimensions can easily be determined for any geometric shape. Sizes and shapes of the systems, and the components thereof, can depend at least on the anatomy of the subject in which the systems will be used, the size and shape of components with which the systems will be used, and the methods and procedures in which the systems will be used.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the system in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special system positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

It will be appreciated that the terms "proximal" and "distal" may be used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" may be used herein with respect to the drawings. However, surgical instruments are used in many orientations and positions, and these spatial terms are not intended to be limiting and absolute.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for calibrating the position of a surgical tool, comprising:
   a surgical tool having an actuator and an end effector, the end effector having at least one target feature, the surgical tool storing a reference data set comprising reference positional information of the at least one target feature;
   at least one imaging device configured to acquire at least one image containing actual positional information of the at least one target feature; and
   a processor configured to
      electronically receive the reference data set from the surgical tool and the actual positional information from the at least one imaging device,
      detect a discrepancy between the actual positional information of the at least one target feature and the reference positional information of the at least one target feature,
      generate a transformation instruction from the discrepancy, the transformation instruction comprising an instruction for the end effector to move based on the detected discrepancy, and
      cause the actuator to move the end effector, based on the transformation instruction, such that the at least one target feature is moved to a reference position embodied by the reference positional information.

2. The system of claim 1, further comprising an electromechanical robotic arm having a tool carrier on a distal end thereof that is configured to couple to a housing of the surgical tool, and wherein the processor is coupled to the electromechanical robotic arm and is configured to control movement of the electromechanical robotic arm and the surgical tool coupled thereto.

3. The system of claim 1, wherein the at least one target feature is selected from the group consisting of a point, a line, a ridge, a joint location, an axis of rotation, a grip position, a surgical tool outline, a surgical tool form, a surgical tool edge, a surgical tool surface, a surgical tool shape, a surgical tool region color, a fiducial, a laser marking, a pad printed marking, a molded element, and a machined element.

4. The system of claim 1, wherein the processor is coupled to the imaging device and is configured to cause the imaging device to acquire images containing actual positional information of the at least one target feature.

5. The system of claim 1, wherein the end effector is selected from the group consisting of forceps, graspers, a needle driver, a clamp, scissors, an electrocautery tool, a circular stapler, a box stapler, a clip applier, a suction tool, an irrigation tool, a linear stapler, a suture stitching device, and a vessel sealer.

6. The system of claim 1, wherein the at least one target feature comprises two target features on the end effector.

7. The system of claim 1, wherein the surgical tool comprises a first surgical tool and the reference data set comprises a first reference data set comprising reference positional information of the at least one target feature of the first surgical tool, and the system further includes a second surgical tool having at least one target feature and a second reference data set comprising reference positional information of the at least one target feature of the second surgical tool.

8. The system of claim 7, wherein the first reference data set differs from the second reference data set.

9. A method of calibrating a position of an end effector of a surgical tool, comprising:
coupling a surgical tool to a surgical robotic system such that a reference data set comprising reference positional information of at least one target feature on an end effector of the surgical tool is transmitted from the surgical tool to a processor of the surgical robotic system, the processor performing a calibration test comprising obtaining at least one image containing actual positional information of the at least one target feature on the end effector,
generating a transformation function based on the reference positional information and the actual positional information, the transformation instruction comprising an instruction for the end effector to move based on a discrepancy between the reference positional information and the actual positional information, and
sending the transformation function to the surgical tool to cause an actuator of the surgical tool to reposition the end effector to a repositioned location based on the transformation function, the repositioned location embodied by the reference positional information.

10. The method of claim 9, further comprising, prior to performing the calibration test, positioning the end effector within a body cavity of a patient, and wherein the actual positional information comprises actual positional information of the at least one target feature on the end effector within the body cavity.

11. The method of claim 9, wherein the at least one target feature on the end effector is selected from the group consisting of a point, a line, a ridge, a joint location, an axis of rotation, a grip position, a surgical tool outline, a surgical tool form, a surgical tool edge, a surgical tool surface, a surgical tool shape, a surgical tool region color, a fiducial, a laser marking, a pad printed marking, a molded element, and a machined element.

12. The method of claim 9, further comprising decoupling the surgical tool from the surgical robotic system, and coupling a second surgical tool to the surgical robotic system such that a second reference data set, that differs from the first reference data set, is transmitted from the surgical tool to the surgical robotic system.

13. The method of claim 9, further comprising obtaining at least one post-calibration image containing post-calibration location information of the at least one target feature and confirming that the post-calibration location information is the same as the reference positional information.

* * * * *